US009533092B2

(12) United States Patent
Gyrn

(10) Patent No.: US 9,533,092 B2
(45) Date of Patent: Jan. 3, 2017

(54) BASE PART FOR A MEDICATION DELIVERY DEVICE

(75) Inventor: Steffen Gyrn, Ringsted (DK)

(73) Assignee: UNOMEDICAL A/S, Birkeroed (DK)

(*) Notice: Subject to any disclaimer, the term of this patent is extended or adjusted under 35 U.S.C. 154(b) by 0 days.

(21) Appl. No.: 13/388,407

(22) PCT Filed: Aug. 6, 2010

(86) PCT No.: PCT/EP2010/061497
§ 371 (c)(1),
(2), (4) Date: Apr. 5, 2012

(87) PCT Pub. No.: WO2011/015659
PCT Pub. Date: Feb. 10, 2011

(65) Prior Publication Data
US 2012/0184909 A1    Jul. 19, 2012

Related U.S. Application Data

(60) Provisional application No. 61/232,115, filed on Aug. 7, 2009.

(30) Foreign Application Priority Data

Aug. 7, 2009  (EP) ..................... 09167445

(51) Int. Cl.
*A61M 5/142* (2006.01)
*A61M 5/158* (2006.01)
(Continued)

(52) U.S. Cl.
CPC ...... *A61M 5/14248* (2013.01); *A61B 5/14532* (2013.01); *A61B 5/6833* (2013.01);
(Continued)

(58) Field of Classification Search
CPC .......... A61B 5/155; A61M 2005/1585; A61M 2005/1586; A61M 2005/14252; A61M 5/14248
(Continued)

(56) References Cited

U.S. PATENT DOCUMENTS 1,592,462 A   7/1926  MacGregor
2,047,010 A   7/1936  Dickinson
(Continued)

FOREIGN PATENT DOCUMENTS

DE    4 342 329 A1   6/1994
DE    196 31 921 A1  3/1997
(Continued)

OTHER PUBLICATIONS

International Search Report completed Dec. 17, 2010 for International Application No. PCT/EP2010/061497.
(Continued)

*Primary Examiner* — Kevin C Sirmons
*Assistant Examiner* — Benjamin Koo
(74) *Attorney, Agent, or Firm* — Wilson Sonsini Goodrich & Rosati

(57) ABSTRACT

The invention concerns a base part for a medication delivery device, the base part comprising a connection part and a moveable part. The moveable part, which moves relative to the connection part, is capable of guiding fluid paths from a medication delivery port to a first cannula or sensor and a second cannula or sensor. The base part also comprises guiding means which can direct each cannula or sensor to its subcutaneous position.

9 Claims, 16 Drawing Sheets

(51) Int. Cl.
  *A61B 5/145* (2006.01)
  *A61B 5/00* (2006.01)
  *A61M 5/172* (2006.01)

(52) U.S. Cl.
  CPC ......... *A61B 5/6849* (2013.01); *A61M 5/1723* (2013.01); *A61B 2560/0412* (2013.01); *A61M 2005/14252* (2013.01); *A61M 2005/1585* (2013.01); *A61M 2005/1726* (2013.01); *A61M 2230/201* (2013.01)

(58) Field of Classification Search
  USPC .............. 604/67, 176–206, 164.12, 535, 173
  See application file for complete search history.

(56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A * | 7/1988 | Konopka et al. ........ 604/167.02 |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,160,315 A | 11/1992 | Heinecke et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |

(56) References Cited

U.S. PATENT DOCUMENTS

| | | |
|---|---|---|
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,629 A | 5/1996 | Heinecke et al. |
| 5,520,654 A | 5/1996 | Wahlberg |
| 5,522,803 A | 6/1996 | Teisson-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A * | 1/2000 | Fischell et al. ............... 604/180 |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A * | 4/2000 | Jacobsen ............ A61M 5/14248 604/140 |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,283,744 B1 | 9/2001 | Edmondson et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Van Lunduyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |

(56) References Cited

U.S. PATENT DOCUMENTS

| | | |
|---|---|---|
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,331,939 B2 | 2/2008 | Fangrow, Jr. |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,713,258 B2 | 5/2010 | Adams et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 8,323,250 B2 | 12/2012 | Chong et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0095138 A1 | 7/2002 | Lynch et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |

(56) References Cited

U.S. PATENT DOCUMENTS

| | | |
|---|---|---|
| 2004/0044306 A1 | 3/2004 | Lynch et al. |
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1* | 8/2004 | Bengtsson .............. 604/136 |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0129691 A1 | 6/2007 | Sage, Jr. et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0004515 A1 | 1/2008 | Jennewine |
| 2008/0058692 A1 | 3/2008 | Propp et al. |
| 2008/0119707 A1 | 5/2008 | Stafford |
| 2008/0200897 A1 | 8/2008 | Hoss et al. |
| 2008/0269687 A1 | 10/2008 | Chong |
| 2008/0312601 A1 | 12/2008 | Cane' |
| 2009/0062767 A1 | 3/2009 | Van Antwerp et al. |
| 2009/0118592 A1 | 5/2009 | Klitgaard |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0028982 A1 | 2/2011 | Lacy |
| 2011/0054399 A1 | 3/2011 | Chong et al. |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0 272 530 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |

(56) References Cited

FOREIGN PATENT DOCUMENTS

| | | |
|---|---|---|
| EP | 0714631 B1 | 6/1996 |
| EP | 0744183 A2 | 11/1996 |
| EP | 0747006 A1 | 12/1996 |
| EP | 0775501 B1 | 5/1997 |
| EP | 0799626 A1 | 10/1997 |
| EP | 0937475 A2 | 8/1999 |
| EP | 0956879 A1 | 11/1999 |
| EP | 1086718 A1 | 3/2001 |
| EP | 1125593 A1 | 8/2001 |
| EP | 1329233 B1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2272559 A1 | 1/2011 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO 99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A1 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/033702 A1 | 3/2008 |
| WO | WO 2008/048631 A1 | 4/2008 |
| WO | WO 2008/052545 A1 | 5/2008 |
| WO | WO 2008/065646 A1 | 6/2008 |

(56) References Cited

FOREIGN PATENT DOCUMENTS

| WO | WO 2008/092782 A1 | 8/2008 |
|---|---|---|
| WO | WO 2008/092958 A2 | 8/2008 |
| WO | WO 2008/092959 A1 | 8/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/080715 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |
| WO | WO 2012/107440 A1 | 8/2012 |
| WO | WO 2012/123274 A1 | 9/2012 |

OTHER PUBLICATIONS

Written Opinion completed Dec. 17, 2010 for International Application No. PCT/EP2010/061497.
"Why inset®?" inset® infusion set product overview; http://web.archive.org/web/20040906102448/http://www.infusion-set.com/Default.asp?ID=108; two pages.

* cited by examiner

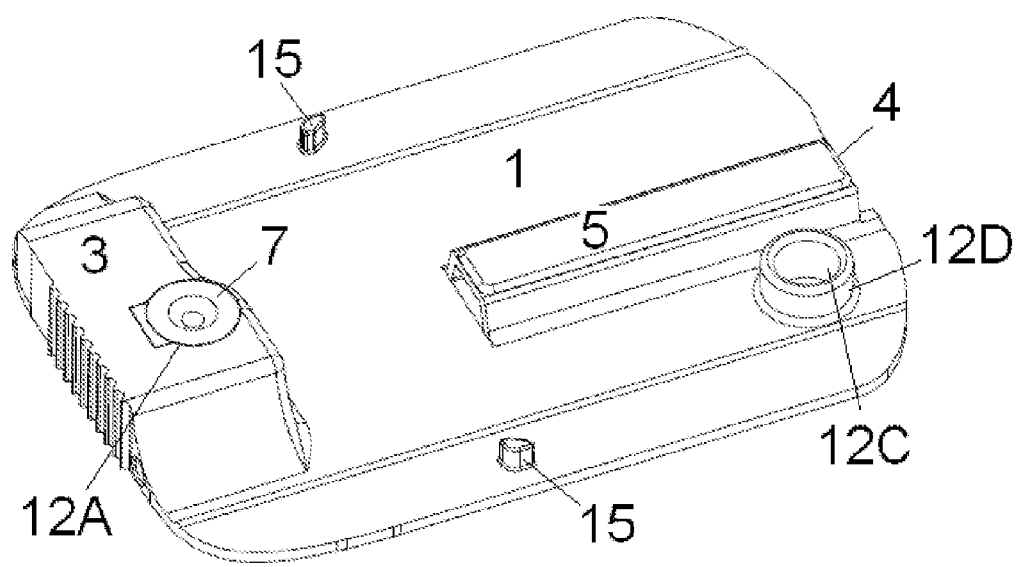
Fig. 1A
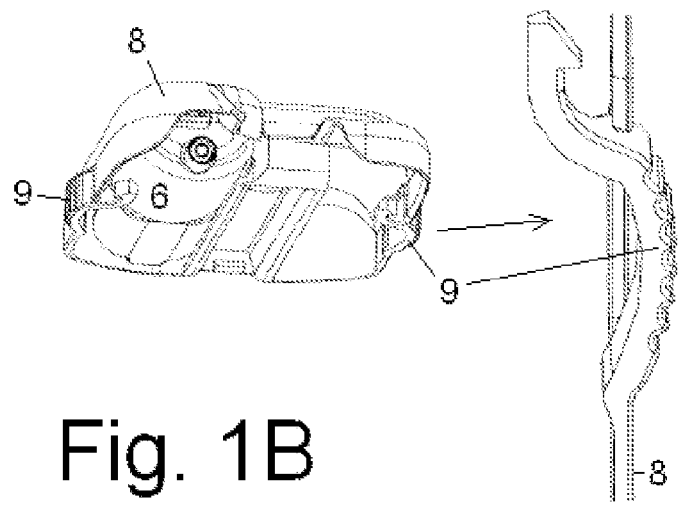
Fig. 1B
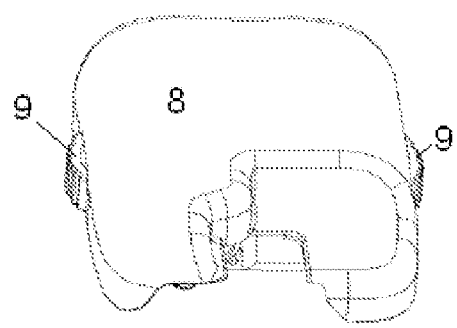

BASE PART FOR A MEDICATION DELIVERY DEVICE

This application claims the benefit under 35 U.S.C. §371 of International Application No. PCT/EP2010/061497, filed Aug. 6, 2010, which claims the benefit of European Patent Application No. 09167445.7, filed Aug. 7, 2009, and U.S. Provisional Application Ser. No. 61/232,115, filed Aug. 7, 2009, which are incorporated by reference herein in their entirety.

The invention concerns a base part for a medication delivery device. The base part is during use fastened to a patient's skin and connected to a separate cannula part which cannula part is positioned at least partly subcutaneous. The base part is also connected to a sensor unit which can detect one or more components e.g. glucose content in the patients blood.

BACKGROUND OF THE INVENTION

The document US 2009/0118592 discloses (FIG. 28C, example 4, page 14) a medical drug delivery device comprising a transcutaneous device unit and a reservoir unit in combination with a Blood Glucose Meter (820), a Continuous blood Glucose Meter (816) and a wireless remote control unit (830) comprising an infusion calculator which parts together form a system (802). A transcutaneous sensor (817) can be formed as part of the transcutaneous device unit and the sensor electronics adapted to process and/or transmit the sensor data is formed as part of the reservoir unit. The sensor can be replaced together with the transcutaneous device or independently thereof.

The document US 2008/0200897 discloses an infusion device an integrated infusion device and analyte monitoring system. This document provides several methods and systems for modular combination of medication delivery and physiological condition monitoring.

Neither of the devices allows for subcutaneously positioned units such as cannulas and sensors can be pointed in different directions when positioned on one single patch or mounting surface and neither of the devices allows for retraction of a cannula without removing the base part or patch which the cannula(s) are part of.

US 2004/0162521 discloses a needle device comprising a housing, a base portion having a mounting surface adapted for application to the skin of a patient and a plurality of needles. Each needle comprises a distal pointed end adapted to penetrate the skin of a patient and each needle has a first position in which the distal end is retracted relative to the mounting surface and a second position in which the distal end projects from the mounting surface. A needle device according to this document being mounted on the patients has to have a height at least corresponding to the length of a needle as the needles before and after use are retracted in their full length perpendicular to the mounting surface, also the cannulas according to the shown embodiments have to be hard, self-penetrating cannulas provided with a side inlet opening.

US 2008/0004515 discloses an integrated analyte monitoring system combined with an on-body patch pump provided with multiple cannulas and a sensor combination. In accordance with an embodiment of this document a first cannula can be configured for transcutaneous delivery of a medication at a first infusion site for an initial time period of e.g. three to four days. Thereafter the first cannula is retracted from the infusion site under the control and operation of one or more controller and infusion management units. After retraction of the first cannula, a second cannula can be inserted at a second infusion site. The second cannula may be inserted automatically by using an insertion device such as an insertion gun configured to couple to the second cannula e.g. including a spring bias driven insertion mechanism. The second cannula (290) is mounted on a base part separate from the patch pump (210) in connection with which the first cannula is mounted.

SUMMARY OF THE INVENTION

The current invention provides an assembly comprising an insertion device for subcutaneously introduction of a penetrating member, where a "penetrating member" is understood to be a needle, a cannula, a sensor or the like. The penetrating member is normally prior and during insertion kept in a position where it is not visible to the patient and where it can not get in contact with the user or the patient before it is actually inserted.

The object of the invention is to provide a base part to be combined with a detachable reservoir/delivery part, the base part comprising fastening means which fastening means releasably attach the reservoir/delivery part to the base part during use and a first fluid path or means corresponding to a first fluid path from a reservoir permitting a flow of fluid between the reservoir/delivery part and the base part when the reservoir/delivery part is attached to the base part, the first fluid path comprises means for interrupting the fluid flow when the detachable reservoir/delivery part is not attached to the base part and opening the fluid path when the delivery part is attached to the base part, the base part also comprises a lower mounting surface and one or more openings through which two or more subcutaneous units in the form of at least one cannula and at least one sensor part or at least two cannulas extend, a second fluid path permitting a flow of fluid from the outlet of the first fluid path to an inlet of a subcutaneously positioned cannula during use, and a signal path is provided from the reservoir/delivery part to a sensor contact part, wherein the second fluid path is in fluid connection with an end opening of a subcutaneously positioned cannula during use.

The end opening connecting to the second flow path being an end opening which is placed above the patient's skin during use. The construction of the base part according to claim 1 allows for the use of soft cannulas although it does not exclude the use of hard cannulas. In some of the illustrating embodiments hard cannulas are used and in some of the embodiments soft cannulas which normally are inserted with an insertion needle are used. The flat base part with openings allows for the use of a separate inserter which can be removed from the base part after mounting of the subcutaneously position units. Secondly, it is difficult to provide a fluid path by a side opening in a soft unsupported cannula i.e. no rigid walls supports the circumference of the soft cannula as the soft walls might move in a longitudinal direction or might give in to fluid pressure which might reduce inner diameter of the cannula.

Definition of end opening: a cannula consists of an elongated tube-shaped piece made by either a soft and flexible material such as elastomer or a hard and rigid material such as metal or hard plastic and this elongated tube-shaped piece can have two end openings: an inlet opening and an outlet opening. If the cannula is of the sprinkler type it might have one or more side outlet openings as well. If the cannula at one end is provided with a part having an extended diameter such as a hub which e.g. is normally used when fastening a moulded cannula inside a holding body of a hard material, this hub is not considered to the part of the elongated tube-shaped piece.

According to an embodiment of the base part the first fluid path can be formed by a connector needle either being part of the base part or a connector needle being part of the reservoir/delivery part and a corresponding entrance for the connector needle on the other part which entrance is normally protected by a protective sealing membrane.

The first fluid path is interrupted when the delivery part is detached and moved away from the base part as at least a sealing membrane covering the outlet of the reservoir is self-closing and upon retraction of the connector needle from the membrane, the membrane will prevent fluid from flowing from the reservoir to the second fluid path. This of cause is only the case when the same reservoir is mounted several times. Often, the protective membranes are covering both the outlet of the reservoir as well as the inlet of the second fluid path of the base part.

According to an embodiment of the base part the second fluid path includes one surface opening surrounded with a gasket having a central opening through which fluid can flow, and a second surface opening surrounded with a hard smooth surface. The second fluid path can comprise a movable part which movable part has at least two different positions each position providing a separate second fluid path connecting the first fluid path to a given cannula.

According to an embodiment of the base part the delivery part has more than one fastening position relative to the base part and each position forms a second fluid path different from all others.

According to an embodiment of the base part one or more of the cannula parts comprise a body of a hard and rigid material having a fluid inlet and a fluid outlet, the fluid outlet from the body corresponding to the inlet end of a cannula. The cannula of the cannula part can e.g. be made of a soft and flexible material such as an elastomer and the hard body of the cannula part can be provided with a top opening.

When the cannula is soft and flexible it is necessary to insert the cannula with an insertion needle which normally passes through a top opening in the hard body i.e. an opening placed opposite and in extension of the tube-shaped cannula which top opening is protected by a septum i.e. a self-closing membrane. According to this embodiment the base part can comprise attachment member for an inserter in connection with each opening and position and fastening means adapted for fastening of each cannula or cannula part or sensor part which is inserted after mounting the base part on the patient's skin. E.g. one cannula and one sensor is inserted e.g. simultaneously through the opening(s) in and attached to the base part on day 0, normally at least one inserter is normally attached to the base part during the manufacturing procedure and when the user receives a device including the base part, the device comprises both a base part comprising a mounting surface and an inserter releasably attached to the base part in a ready-to-use position. The attachment member for the inserter allows for the user to remove the insertion needle e.g. together with remains of inserter after inserting the cannula and/or sensor. Therefore no penetrating needle is necessarily mounted during use, instead only soft cannulas or soft sensor parts are mounted subcutaneously during use, this is more comfortable for the patient.

The current invention might provide an assembly comprising an insertion device for subcutaneously introduction of a penetrating member, where a "penetrating member" is understood to be a needle, a cannula, a sensor or the like. The penetrating member is normally prior and during insertion kept in a position where it is not visible to the patient and where it can not get in contact with the user or the patient before it is actually inserted.

The object of the invention is to provide a base part comprising or being connectable to at least one cannula to be placed subcutaneously which base part also comprises
  a contact or mounting surface for fastening the base part to a patients skin,
  fastening means (4) connecting medication supply (6) or the like to the base part during use,
  a sensor and/or transmitter unit,
wherein at least one cannula is attached to or comprises retraction means which retraction means make it possible to remove the at least one cannula from its subcutaneous use position and retract the cannula(s) to a position where it is not engaged with the patients skin. The base part can comprise or be connectable to at least two cannulas.

According to one embodiment the at least two cannulas are placed with a distance $I_1$ of at least 10 mm between each other, normally with a distance $I_1$ of at least 20 mm between each other.

According to an embodiment the base part comprises a connection part being a part of the base part which connection part comprises a fluid connection having at least one inlet opening and at least one outlet opening where the inlet opening forms a fluid connection to a medication supply or the like and the second opening forms a fluid connection to a cannula part. The connection part is stationary relative to the mounting surface and the base part further comprises a movable part which movable part can move relative to the connection part and the mounting surface comprises at least two separated fluid paths where one fluid path guides fluid to a first cannula and the second fluid path guides fluid to a second cannula. The base part can comprise guiding means where each guiding means guides a subcutaneously placed part to its fully forward i.e. subcutaneous position. Further, the guiding means can direct each subcutaneous positioned part to cut through the patients skin in a direction which deviates 15-85° from a direction parallel to the patients skin surface at the area where the mounting surface is attached during use.

According to one embodiment the at least one of the cannula parts is a separate part which has to be inserted and fastened to the base part before the base part can transfer fluid to the patient.

According to one embodiment the sensor part is a separate unit which has to be inserted and fastened to the base part before it is possible to establish a measurement of the desired parameter.

According to one embodiment the sensor part measures glucose or an analyte corresponding to glucose and the medication delivered through the at least one cannula is insulin.

According to another aspect of the invention, the invention relates to a system comprising a base part according any of the preceding claims and a delivery device which can be attached to and worn by the patient together with the base part which delivery device comprises a reservoir containing fluid, pumping means for transferring fluid from the reservoir to the base part, and a power source which power source provides power to both the pumping means and to the sensor of the base part.

Another object of the invention is to provide a base part being connectable to a separate cannula part and comprises means for receiving a separate cannula part, the base part comprising
  a contact surface for fastening the base part to a patients skin, fastening means connecting medication supply (6) or the like to the base part during use, a connection part being a part of the base part which connection part comprises a fluid connection having at least a first and a second opening, i.e. an inlet and an outlet, where the first opening forms a fluid connection to a medication supply or the like and the second opening forms a fluid connection to a separate cannula part, which base part is connectable to or comprise a sensor unit, and wherein the connection part is rigid and each opening of the fluid connection is either provided with a sealing or adapted to fit with a corresponding sealing of an adjacent part.

DEFINITIONS

"Parallel" or "essentially parallel" as used herein refers to a second movement in a direction, plane, item or the like defined in relation to a first or a reference plane or direction which reference plane or direction has a direction defined as the angle $\alpha=0°$; and the second plane or direction deviates at maximum $\pm 10°$; normally not more than $\pm 5°$ from the first or reference direction $\alpha$.

In the context of the application "horizontal" or "essentially horizontal" means that a movement in a direction, a direction, plane, item or the like is horizontal or essentially horizontal is parallel or essentially parallel to the surface of the skin of a patient as defined above. For example, the base part to which the insertion device is fastened can be horizontal, or essentially horizontal, parallel or essentially parallel to the skin.

"Perpendicular" or "essentially perpendicular" as used herein refers to a second movement in a direction, a direction, plane, item or the like defined in relation to a reference plane or direction which reference plane or direction has a position or a direction in the angle $\beta=0°$; and the second plane or direction deviates between 80-100°; normally between 85-95° from the first reference R.

In the context of the application "Transversal" or "essentially transversal" can be used interchangeably with perpendicular or essentially perpendicular as defined above.

"Means": As used herein, the expression "means" can comprise one or more means. This is irrespective, if with respect to grammar, the verb relating to said means indicates singular or plural.

BRIEF DESCRIPTION OF THE DRAWINGS

A detailed description of embodiments of the current invention will be made with reference to the accompanying figures, wherein like numerals designate corresponding parts in different figures.

FIG. 1A shows an embodiment of a base part according to the invention which base part is provided with an opening for a cannula part and an opening for a sensor part.

FIG. 1B shows an embodiment of a delivery part corresponding to the embodiment of a base part in FIG. 1A.

DETAILED DESCRIPTION OF THE INVENTION

Figure 2:
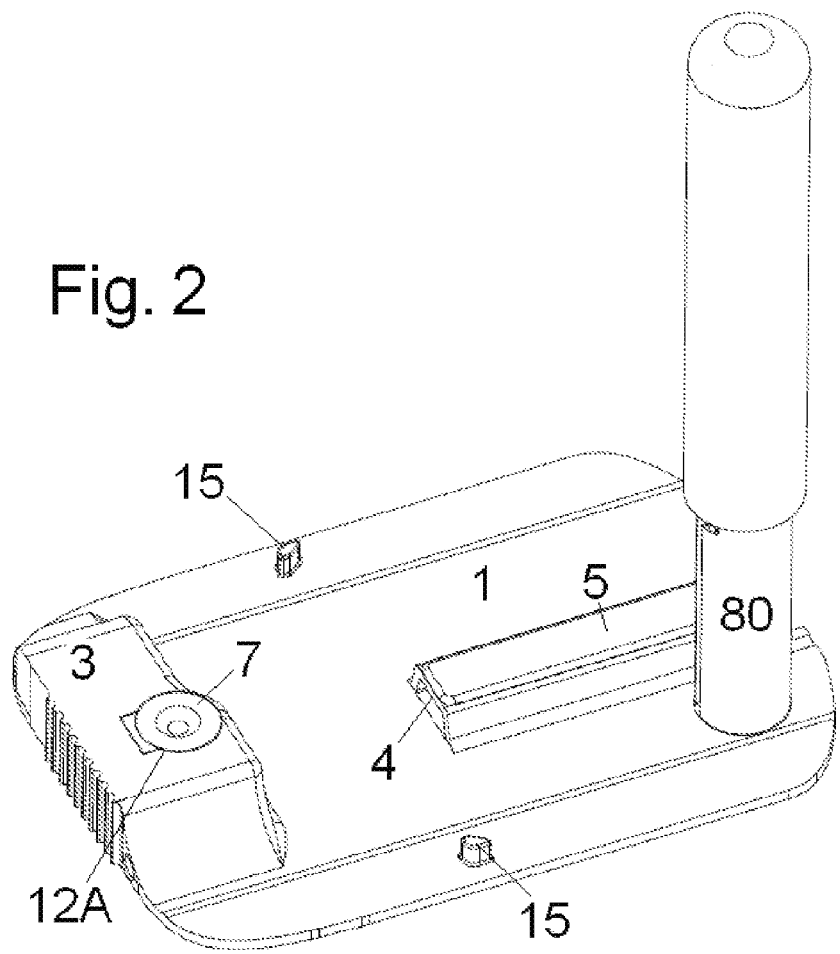
FIG. 2 shows the same embodiment of a base part as FIG. 1 combined with an inserter for inserting a sensor part.

FIG. 1 A shows an embodiment of a base part 1 comprising one through going opening 12A for a cannula part 7 and one through going opening 12C for a sensor part. The cannula part 7 is mounted in the through going opening in FIG. 1A and the top surface of the cannula part 7 provided with a centrally positioned septum can be seen. The base part 1 comprises a flat surface having a lower side, the lower side being in touch with the patients skin during use, is provided with a mounting surface; normally the mounting surface will consist of a pressure adhesive layer either welded to the lower side of the base part 1 or adhered directly to the lower side of the base part 1. The upper side of the base part 1 comprises fastening means 15 having the form of two protruding parts which fastening means 15 in combination with longitudinal raised guiding means 4 keeps a delivery part 8 in position during use.

The base part can e.g. deliver insulin based on a measurement of glucose in the patient's blood.

The sensor part is not shown in FIG. 1 i.e. the base part 1 is in a state (pre-use) where the sensor has not yet been positioned in the opening 12C. According to the embodiment of FIG. 1 the sensor opening 12C is provided with attachment member for an inserter in the form of a cylindrical wall 12D standing upright relative to the flat surface of the base part 1. The upright or protruding cylindrical wall functions as attachment member for a sensor part inserter when positioning the sensor part as exit end of the sensor part inserter fits tightly around the cylindrical walls 12D.

The attachment member 12D used to position the sensor part might have other shapes e.g. the attachment member 12D can have the form of on or more upright stick(s) or bar(s), or one or more openings into the surface of the base plate 1.

The opening 12C for the sensor is placed at the opposite end of the surface plate 1 relative to the opening 12A for the cannula part 7. This ensures that the interference between medication input and a measurement of a physiological effect of the medication is as small as possible. A necessary minimum distance between the two points i.e. the point of inflow of medication and the point of measurement of a physiological effect relating to the decomposition of medication, will depend both on the kind of medication and concentration of the medication which is supplied to the patient and also of which subcutaneous depth each of the two points are positioned in. Often a distance of at least 20 mm between the two points will be acceptable. FIG. 1B shows a delivery part 8 corresponding to the base part 1 of FIG. 1A. From the of the lower side it is possible to see how a reservoir 6 can be positioned in the delivery part 8 and to see how two opposite positioned release handles 9 corresponding to the fastening means 15 of the base part 1 are placed at the edge of the delivery part 8. Further a longitudinal track corresponding to longitudinal raised guiding means 4 on the base part can be seen. The corresponding means of the delivery part 8 can slide along a metal lining 5 of the guiding means 4 having the form of a raised platform 4 in the longitudinal direction. The metal lining 5 can e.g. be magnetic and provide easy "catching" of the delivery part 8 during mounting of the delivery part 8, if the delivery part 8 is provided with a corresponding magnetic part. When the delivery part 8 arrives at its working position, the two release handles 9 engage respectively with the fastening means 15 in the form of two parts protruding from the upper surface of the upper surface of the base part 1. When the delivery part 8 is in its working position it is locked in all horizontal directions by the release handles 9. The locking mechanisms make it possible to fasten and release the delivery device from the base part as often as needed i.e. a single-use base part can be combined with a multi-use delivery part.

The two release handles 9 are formed as s-shaped bands where one end is fastened hinge-like to the housing of the delivery part 8 and the first curve in the s-shape is slightly extending the outer surface of the housing of the delivery part whereas the second curve is free i.e. not attached to the housing of the delivery part 8 and is provided with a hook-like shape which can fold around the fastening means 15 protruding from the distal surface of the base part 1. When the delivery part 8 is locked to the base part 1 both release handles 9 are folded round the fastening means 15, when the delivery part 8 is to be removed from the base part, the two opposite release handles 9 are pushed together whereby the hook-like parts of the release handles 9 are released from the protruding parts and the delivery part 8 can be moved backwards i.e. in the direction away from the cannula part 7 and removed from the base part in this direction.

In FIG. 1B the delivery part is also shown from above.

In FIGS. 1A and 1B it is not possible to see the inlet opening in the connection part 3 through which e.g. medication from the reservoir 6 can enter, normally the inlet opening is protected with a membrane to prevent contamination with microorganisms. According to one embodiment the connection part 3 is provided with both a connector needle (not shown as it is placed behind the bubble shaped membrane) and a bubble shaped self closing membrane 17 and the reservoir 6 can be provided with a bubble shaped self closing membrane. Hereby a fluid path is established providing transfer of medication e.g. insulin or nutrients from the reservoir to the connector part 3. As both parts are provided with self closing membranes it will be possible to separate the two units from each other and rejoin them at a later time without the connection part 3 and thereby the patient being contaminated.

The present device is especially directed towards use of a subgroup of cannulas known as soft needle cannulas and they have a wide range of applications, e.g. in automated drug delivery devices such as insulin delivery devices. The soft needle cannulas are in general more flexible and softer than other cannulas.

The soft needle cannulas are generally used together with an introducer needle 11, where the needle is used to penetrate the barrier to the body e.g. the skin and assist the introduction of the cannula. The needle is removed after introduction of the cannula into a body cavity. The soft needle cannula is left in the body cavity for a desired period of time in which it functions as the means for drug delivery. The soft needle cannula is removed from the body cavity, by simple withdrawing after end of use.

A soft needle cannula often comprises a tube-shaped flexible part and a hub. The tube-shaped flexible part is adapted for insertion into a patient and it facilitates the fluid transport to or from a body cavity. The tube-shaped part must be flexible in order to allow the carrier of the cannula, e.g. a patient, to move without serious unpleasantness. However it must not be so flexible that it is capable of forming kinks which may stop the drug delivery. The hub is the connecting means on the tube shaped part adapted for connecting the tube shaped part to either the drug delivery devise, to the fluid collecting container or to another connecting means e.g. a second tube. Preferably soft needle cannulas are composed of a material which are sufficiently flexible to bend, when the carrier moves and sufficiently rigid to avoid kinking closing off the drug supply. Further the material must be compatible with medical use i.e. irritation of the skin must be kept at a minimum, being non-toxic it must not decompose in the body, etc. Thermoplastic elastomers (TPE) are a type of material which fulfils these requirements. Examples of such useful elastomers are: polyester ethers, ECDEL, styrene based TPE, olefin based TPE, urethane based TPE, ester based TPE, amid based TPE, polyolefines and silicone rubbers. In a preferred embodiment the material is selected from the group consisting of polypropylene, C-FLEX™, mixtures of C-FLEX™ and polypropylene, LUPOLEN™ 1840H, LUPOLEN™ 3020D, PELLETHANE™ 2363-75D, PELLETHANE™ 2363-55D, TECOTHANE™ and CARBOTHANE™.

According to one embodiment a cannula part can comprise a hard hub or body provided with a cannula and with a protruding front having a flat surface provided with an opening. The protruding front of the cannula part need not be flat; it can actually have any desired shape as long as it is possible to create a corresponding surface on the connection part 3 facing the cannula part. The front can be inclined in such a way that the cross-section at the upper i.e. distal end of the cannula part is larger than the cross-section at the proximal end of the front, i.e. the end closest to the patient after insertion. The opening of the protruding front is an inlet or outlet through which liquid can enter or exit the cannula part. The body is further provided with a top opening which can be covered with a self closing membrane. The top opening need some kind of entrance protection as it is facing an outer surface which is in contact with the surroundings.

The top opening is primarily used when inserting the cannula part if the cannula 22 is a soft cannula. That the cannula is soft means that it is made of a relatively soft material which cannot by itself penetrate the patients skin, in this case it is necessary to use a pointy insertion needle of a relatively hard material when inserting the cannula and this pointy needle can be inserted through the top opening, pass through an inner hollow in the body of the cannula part and further pass through the full length of the cannula in such a way that the pointy end of the insertion needle stick out of the open end of the hollow cannula. After insertion i.e. after the cannula has been placed sub- or transcutaneous in the patient, then the insertion needle is retracted and the cannula is left inside the patient. The cannula part can also provided with fastening means which can have the form of a series of outward hooks being flexibly fastened to the body in such a way that the hooks can pivot inwards toward the centre of the cannula part. When the cannula part is pressed toward the base part, the hooks passes an edge which pushes them toward the centre as they passes the edge and when the hooks have passed the edge they return to their original position and as a upward surface of one or more of the hooks touch a downward surface of the edge the cannula part is locked unreleasably against the edge.

The cannula part might also be provided with a guiding track on opposite sides of the body corresponding to protruding parts on the not shown connection part 3. Further the opening to the top placed septum can be provided with an upright edge helping by providing an injection site if the user want to perform injections of liquid by a syringe.

The fastening means of the cannula part lock the cannula part to the base part at the time where it is fully inserted. The fastening means can comprise outward hooks that can pivot around an axe close to the body of the cannula part in such a way that the diameter formed by the outermost edge of the hooks can be reduced when the hooks are pressed inward i.e. towards the centre of the cannula part. When the pressure is removed the hooks will return to their original position due to the flexibility of the material. The hooks will be pushed inwards when they pass an opening such as e.g. the opening 12B or a corresponding opening in the surface plate having a cross-section which at least in one dimension is smaller than the outer edge of the hooks and as the hooks return to their original position after having passed through the opening, the hooks will lock the cannula part in the inserted position.

The body of the cannula part might also have the shape or profile of a truncated cone i.e. in each horizontal cross-section of the body it is round having varying diameters. The body might then be provided with two permanently attached circular sealings or gaskets. Between these two gaskets is the opening positioned which opening allows for fluid to enter the inner through going opening of the cannula part. The cannula part is to be placed in a part of the base part e.g. the connection part 3 provided with a corresponding cavity 12A also having the shape of a truncated cone. The cavity 12A has an inlet/outlet opening 12 for fluid flowing to or from the cannula.

A sealing has to be provided between the opening in a side surface of the body of the cannula part and the opening 12 of the fluid path of the connection part 3. The sealing can have the form of an O-ring i.e. a cylindrical tube attached to or pushed into the connector part 3 encircling the opening. The sealing can be provided with an inner support which can have the form of a cylindrical tube. When the cannula part is inserted into the opening 12A the sealing might be distorted due to the tight fit of the body of the cannula part as the cannula part will touch and slide along the sealing. This movement can cause the sealing to get pulled out of position and when the sealing is pulled out of position it might either cause liquid to leak or the inserted part to jump back thereby pulling the subcutaneously positioned part away from the desired position. One solution to this problem is to lubricate the sealing e.g. with silicone or otherwise ensure that the sealing is very smooth, a second solution would be to lubricate the part to be Inserted and a third solution would be to provide a bevelled edge below the lower edge of the sealing. Such an opening can be provided by cutting of the edge below the sealing as illustrated in FIG. 28 of the priority document or by cutting of a corner and thereby increasing the distance between the inserted part and the connector part below the sealing by "moving" the surface of the connector part 3 to the left.

FIG. 2 shows the same embodiment of a base part as FIG. 1 but in FIG. 2 an inserter 80 is attached to the attachment member 12D of the opening 12C for the sensor part as the round opening in the sensor inserter at the exit opening can be pushed down towards the surface of the base part through which movement the opening of the sensor inserter 80 is brought into close contact with the attachment member 12D due to friction between the two parts. Several inserters which can be used to insert a sensor part in the base plate according to the invention is e.g. described in the document WO 2008/014792 which was published 7 Feb. 2008, and these inserters are incorporated in the present document by reference.

Figures 3A, 3B:
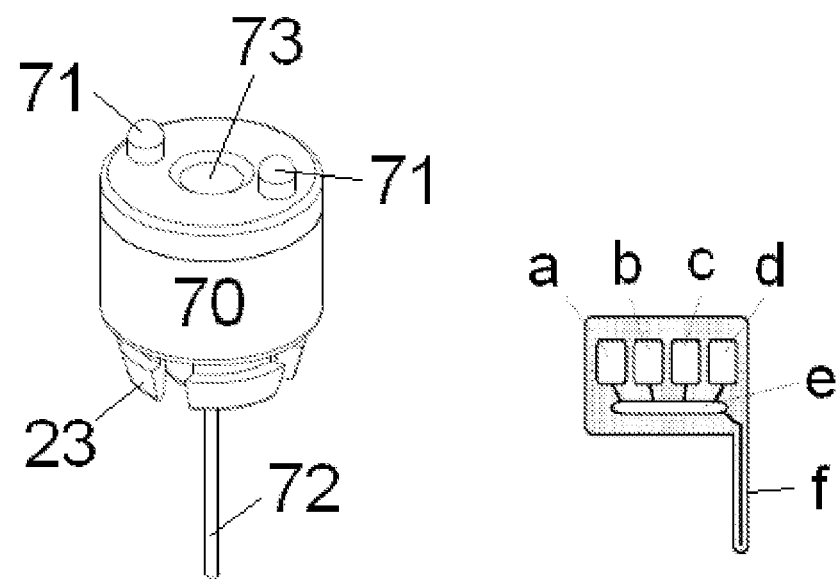
FIG. 3A-3B shows an embodiment of a sensor part which can be used together with the embodiment of the base part shown in FIGS. 1 and 2.

FIG. 3A shows an embodiment of a sensor part which can be used together with the embodiment of the base part 1 shown in FIGS. 1A and 2A. The sensor part comprises a part which is to be placed subcutaneously in the patient; this necessitates the use of an inserter or at least of an insertion needle. If the reading of the sensor part can be made from the surface of the patient's skin instead of subcutaneously this will normally be preferred but for most indicators such as e.g. glucose it is at present recognized that more accurate readings are obtained if the sensor is of a type which has access to the patient's blood.

The sensor part comprises a body 70 having a through-going opening in the longitudinal direction i.e. the direction of insertion. This through-going opening allows for an insertion needle to pass through the body of the sensor part while surrounding the subcutaneous part of the sensor part is protected at the surface end by a septum 73 in order to prevent micro-organisms from entering into the through-going opening from the surface of the device during use. An insertion needle used to insert such a sensor part needs to have an open cross-section e.g. a U-shaped cross-section embracing part of the periphery of the subcutaneous sensor part in stead of completely surrounding the subcutaneous sensor part. The sensor part further comprises two contact points 71 which contact points establish electrical contact with the power source e.g. the battery of the delivery device when the delivery device is fixed to the base part and the unit is in working condition. The battery or power source of the delivery device normally provides power to both the pump delivering fluid from the reservoir to the cannula part and to the sensor part. The delivery device provides the sensor part with current through these contacts. Normally, the power source will send an electrical impulse to the sensor part and the sensor part will react and return a signal i.e. in the form of a voltage as a response to the electrical impulse being transmitted to the sensor part from the power source of the delivery device. Also, the sensor part comprises a protruding sensor unit 72 which is to be inserted subcutaneously during use whereby it can get in contact with the patients blood. This sensor type will register a potential difference over the inserted part and return a signal for the potential difference to the delivery device. The sensor part is provided with retention means 23 of the same type as the cannula part.

Cannula parts 7 which can be used with the base part according to the present invention are known and detailed descriptions of such cannula parts can be seen e.g. in WO 2009/101130 (published 20 Aug. 2009) in the description corresponding to FIG. 4A-4C, FIG. 9A-9B, FIG. 10 and FIG. 13. This description is incorporated herein by reference.

FIG. 3B shows a second embodiment of a sensor part which can be used together with a base part according to the invention. The sensor part comprises a non-conductive part having layers of conductive material placed thereon. The sensor part is formed with a subcutaneous part f which is to be placed subcutaneously and make contact with the patient's fluids. The layers a, b, c and d represents conductive parts through which contact can be made to the delivery device. The layers a, b, c and d can e.g. represent a working electrode a, a guard layer b, a reference electrode c and a counter electrode d. The sensor part can be moulded into a plastic cover which makes it easier to insert in a base part.

Figure 4A:
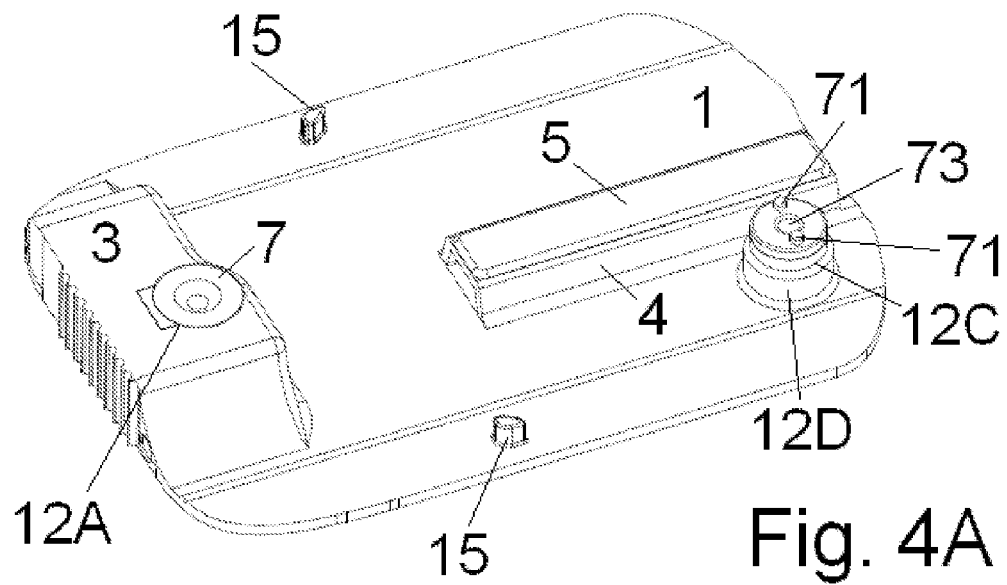
FIG. 4A-B shows two views of the embodiment of the base part of FIG. 1 which has both a cannula part and a sensor part positioned in each there opening.
Figure 4B:
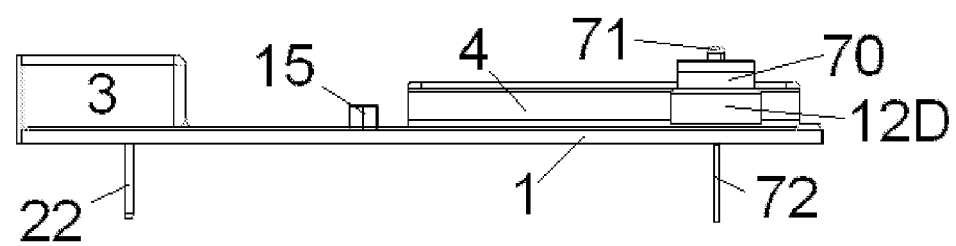

FIG. 4A-B shows two views of the embodiment of the base part of FIG. 1A having both a cannula part 7 and a sensor part positioned in each there opening 12A and 12C. FIG. 4A shows a view from the upper side of the base part i.e. the side facing away from the patients skin and FIG. 4B shows a side view of the base part. The sensor part is partly hidden by the guiding means 12D which guiding means 12D during insertion of the sensor part in the opening 12C helps the user of the inserter to position the inserter 80 in both the correct position and in the correct angle. In FIG. 4B it is possible to see the parts which are positioned subcutaneously during use i.e. the cannula 22 and the sensor unit 72.

Figure 5A:
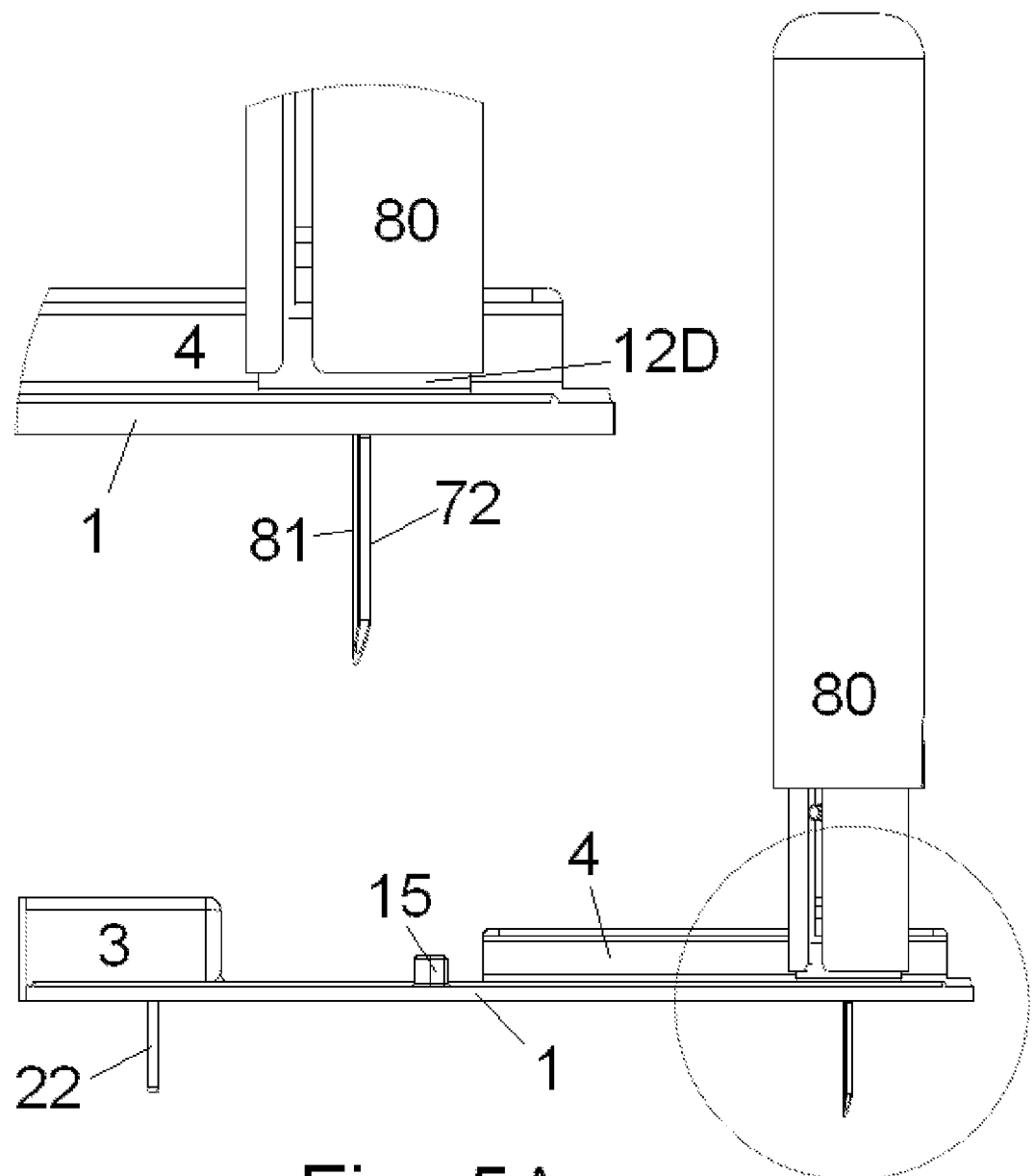
FIG. 5A-C shows the embodiment of the base part of FIGS. 1, 2 and 4 where the sensor part has been inserted subcutaneously and the inserter are still in position on the base part.
Figure 5B:
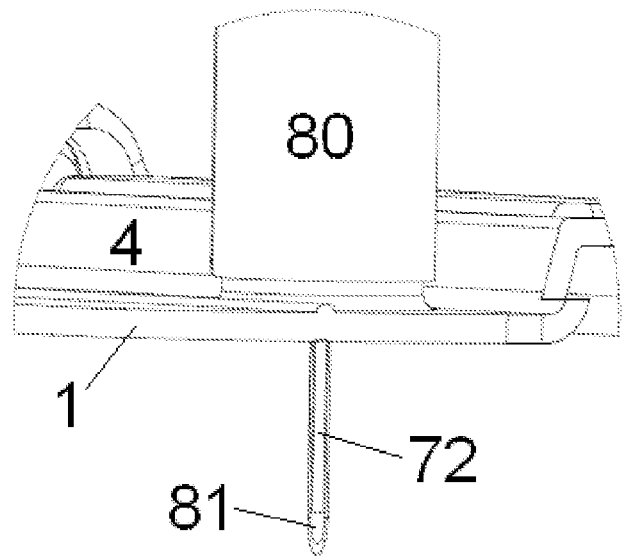
Figure 5C:
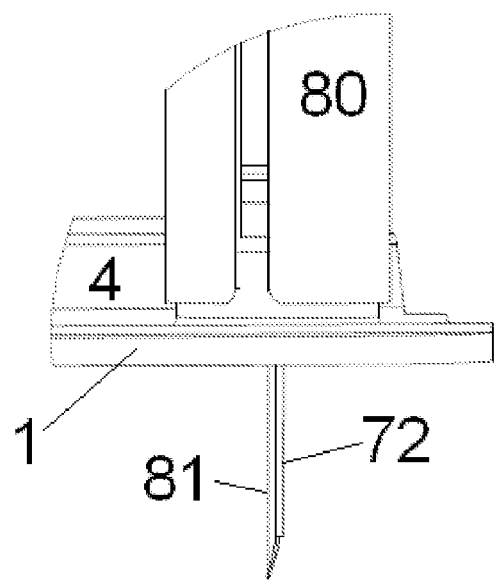

FIG. 5A-C shows the same embodiment of the base part as FIGS. 1A, 2 and 4A. In FIG. 5A-C the sensor part has been inserted subcutaneously by the use of the inserter 80 but the inserter has not been removed from the base part yet. The inserter 80 can be released from the sensor part and will according to this embodiment of the delivery device need to be removed after insertion in order for the user/patient to be able to attach the delivery part to the base part and obtain a fully functional delivery device. FIG. 5A shows the combined device i.e. the base part having the inserter attached to the guiding means 12D of the sensor opening 12C in full size and an enlargement of the combined device which enlargement shows the encircled part of FIG. 5A. In the enlargement it is possible to see that the subcutaneous part relating to the sensor before retraction of the inserter is the combination of a central sensor part 72 which cannot by itself penetrate the patients skin and an insertion needle 81 which partly encircles the central sensor part 72 and which is made of a hard material such as metal or plastic and having a sharp or pointed end. The material of the insertion needle 81 is hard enough to penetrate the patient's skin and provide a subcutaneous position for the softer central sensor part 72. The insertion needle 81 is an unreleasable part of the inserter 80, and when the inserter 80 is removed from the guiding means 12D of the base part the insertion needle 81 is also removed from the subcutaneous position.

FIG. 5B shows the combined device of FIG. 5A in a view from the open side of the insertion needle 81. From this open side it is possible to see the subcutaneous part 72 of the sensor. FIG. 5C shows the combined device of FIG. 5A in a view from the side of the insertion needle 81. From this side it is possible to see a part of the subcutaneous part 72 of the sensor and it is possible to see the sharp inclined tip of the insertion needle 81 which insertion needle 81 has an open cross-section which can be described as a U-shaped cross-section which partly encircles the subcutaneous sensor part 72.

Figure 6A:
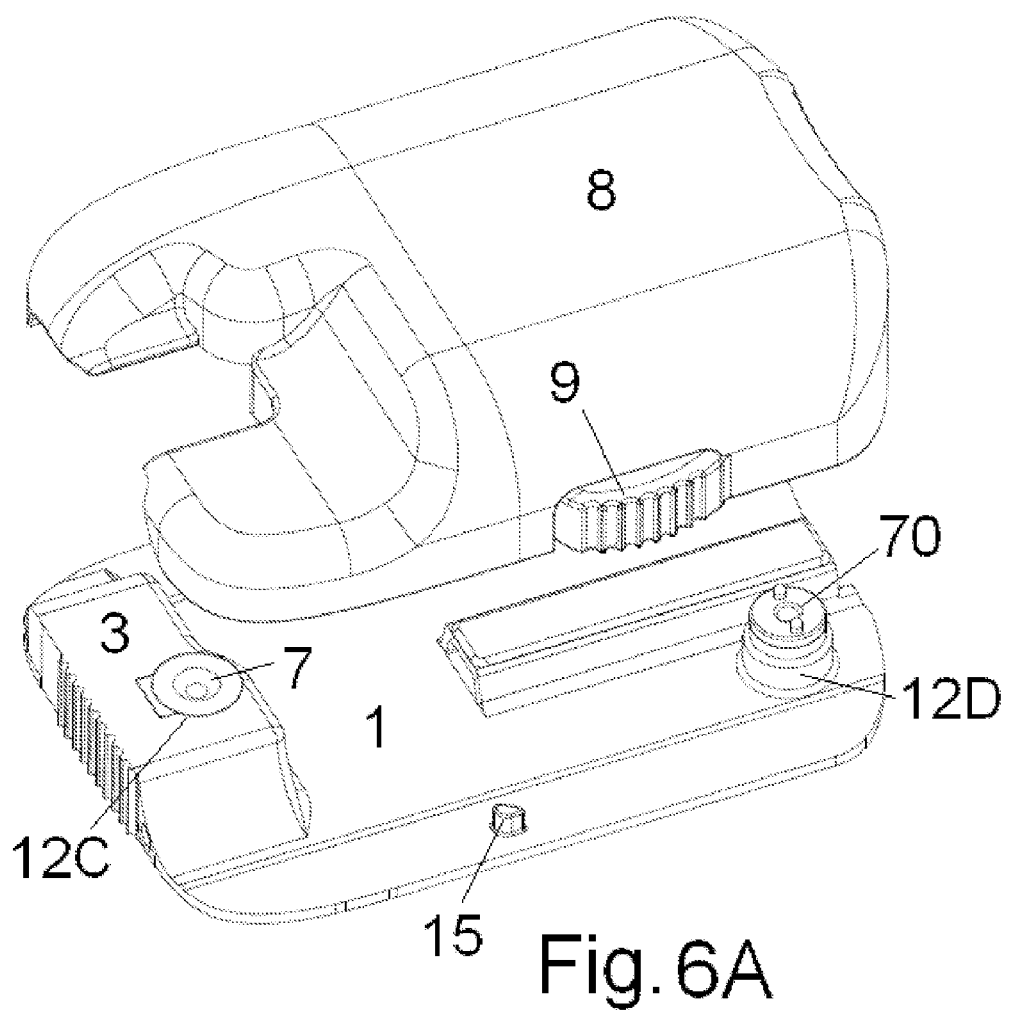
FIG. 6A-B show the embodiment the base part of FIG. 1 together with a delivery part.
Figure 6B:
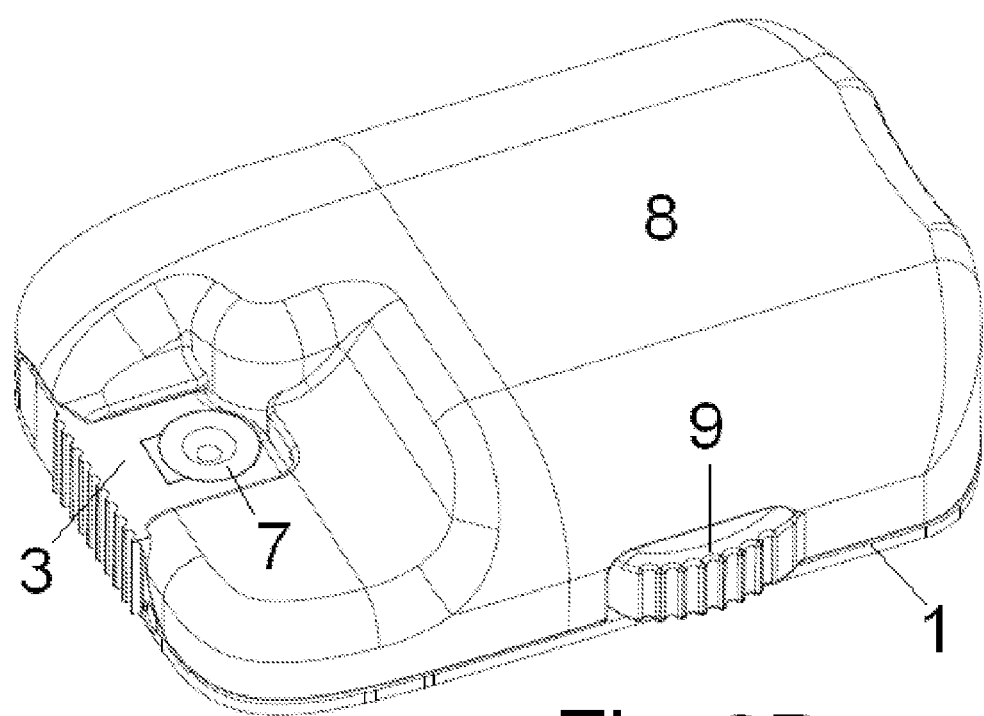
Figure 6C:
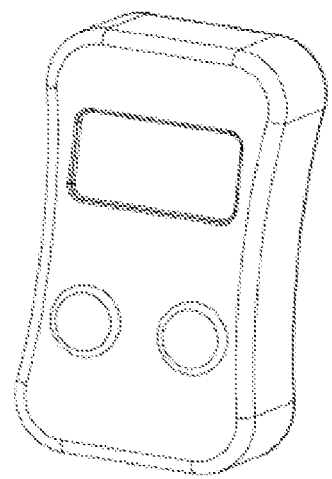
FIG. 6C shows a controller to be used with such a combined delivery device.
Figure 7:
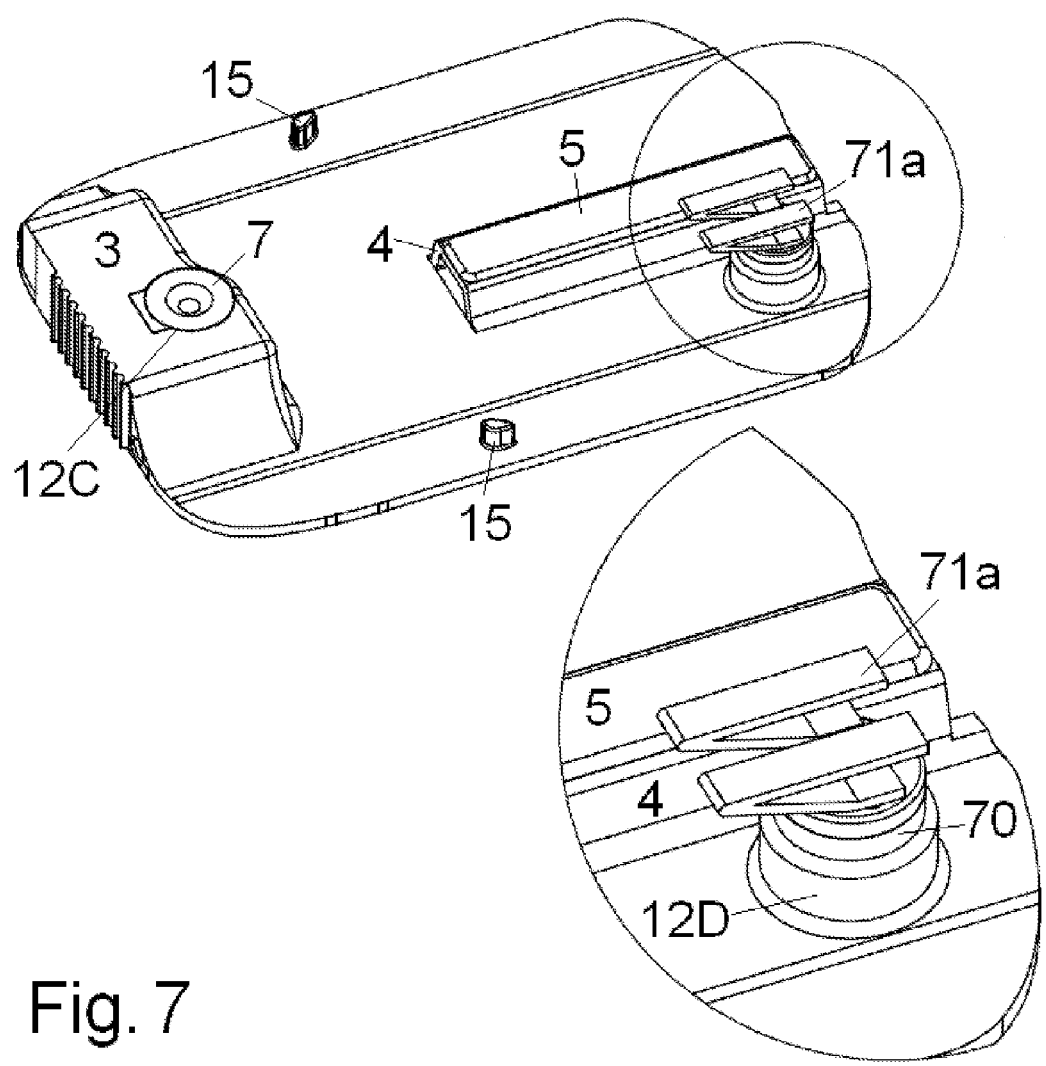
FIG. 7 shows the same embodiment of the base part including a sensor as shown in FIG. 4A-B, the figure further includes an illustration of the position of the contacts of the delivery part during use.

FIG. 6A-B show the embodiment of the base part of FIG. 1A together with a delivery part 8 which delivery part is of the same type as the delivery part 8 shown in FIG. 1B. The delivery part of FIGS. 6A and 6B is described in the text accompanying FIG. 1B. In FIG. 6A the delivery part 8 is seen in a short distance from the base part just above the position where the delivery part will be attached to the base part during use. In FIG. 6B the delivery part is attached to the base part in the use-position. FIG. 6C shows a hand held controller to be used with such a combined delivery device, such a controller will normally be able to receive values read out from the sensor and transmitted by the delivery device. Also, the hand held controller—a PDA (Personal Digital Assistant)—might be able to read in amended set points which can be transmitted to the delivery device and thereby controlling the amount of medication dosed to the patient. This system provides the possibility for having a feedback or closed-loop control system where the measured value of the analyte e.g. glucose is compared to the set point for the analyte and the difference is returned to a controller in the delivery device as an actuating error signal, then a new output signal providing a corrected amount of medication e.g. insulin is calculated in order to reduce the error signal, FIG. 7 shows the same embodiment of the base part including a sensor as shown in FIG. 1A. FIG. 7 further includes an illustration of the contacts 71a of the delivery part which create a contact for current and electrical signals during use i.e. the contacts provides a signal path from the sensor to the delivery part 8. The contacts 71a are unreleasably attached to the delivery device. The existence of the sensor part and the contacts 71a makes it possible to control the amount of delivered medication in a dosed loop as the sensor part can provide a signal indicating whether a set point is reached. The contacts 71 has the form of a V where one leg of the V is connected unreleasably to the delivery part and the other leg of the V is pressed against the contacts of the sensor part when the delivery part slides into use position during mounting on the base part.

Figure 8:
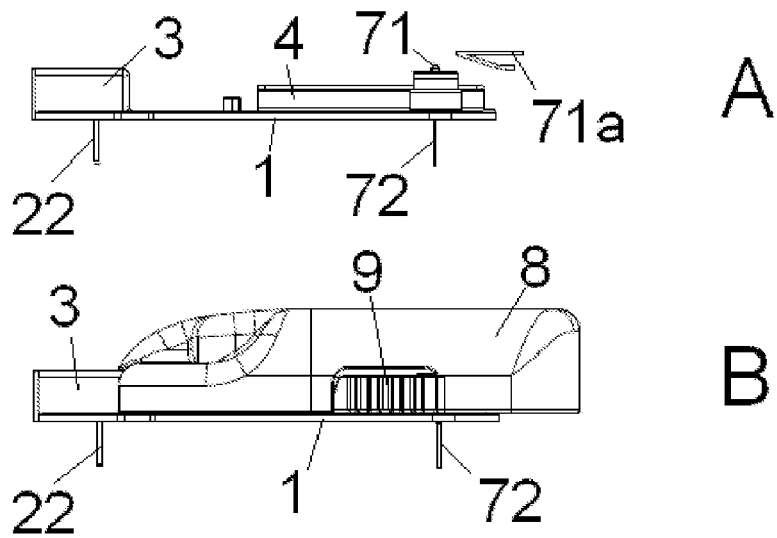
FIG. 8 shows the same embodiment as FIG. 7 including the contacts 71a of the delivery device where the delivery device is in a pre-use position.

FIG. 8A shows the same embodiment as FIG. 7 including the contacts 71a of the delivery device. The side view of FIG. 8A illustrates the position of the contacts 71a relative to the base part in a position before the use where the delivery device is ready to slide over the guiding means 4 of the base part in order to establish a fluid contact between the reservoir of the delivery part and the connecting part 3 of the base part. FIG. 8B shows the actual position of the delivery part relative to the base part when the device is in a pre-use position where the contact is in the position of FIG. 8A.

Figure 9:
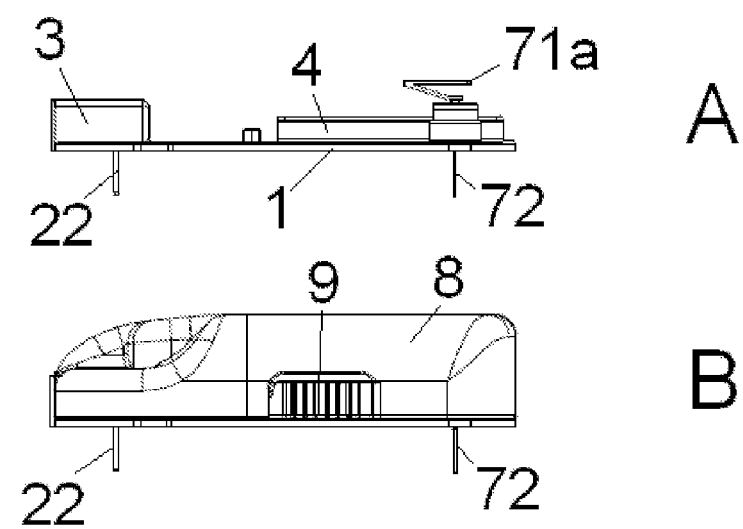
FIG. 9 shows the same embodiment as FIG. 7 including the contacts 71a of the delivery device where the delivery device is in a use position.

FIG. 9A shows the same embodiment as FIG. 7 including the contacts 71a of the delivery device. The side view of FIG. 8A illustrates the position of the contacts 71a relative to the base part in a use position where the delivery device has been sliding over the guiding means 4 of the base part and has established a fluid contact between the reservoir of the delivery part and the connecting part 3 of the base part.

FIG. 9B shows the actual position of the delivery part relative to the base part when the device is in a use position where the contact is in the position of FIG. 9A.

Figure 10:
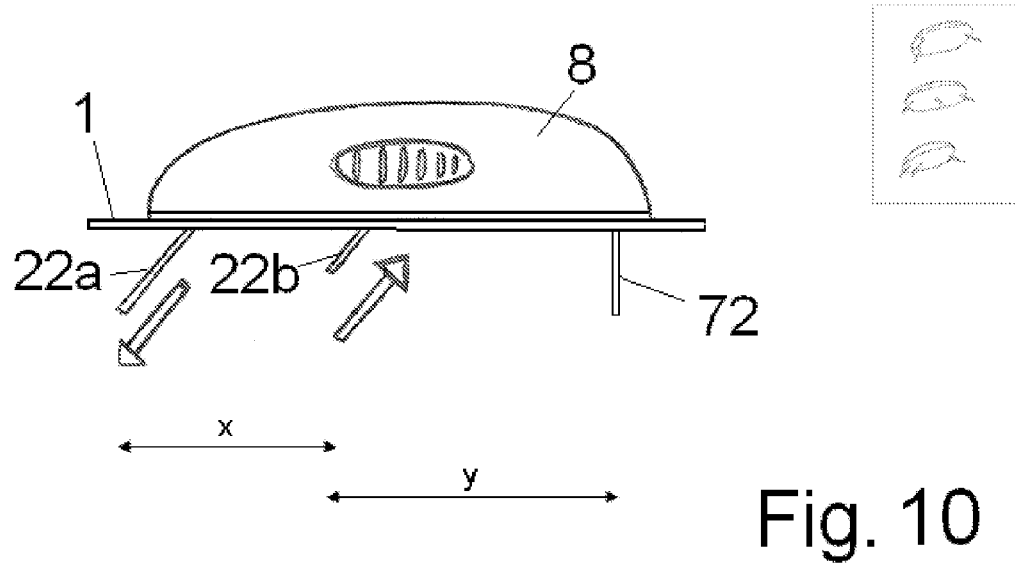
FIG. 10 shows an embodiment of a base part having two separate cannulas and a sensor placed subcutaneously.

FIG. 10 shows an embodiment of a base part 1 having two separate cannulas 22a and 22b. The base part has an oval shape and the two subcutaneous cannulas can either be placed beside each other at one end of the oval shaped base part or displaced relative to each other along the longitudinal axis of the oval shaped base part. In order to increase the distance between the outlets of the cannula, the cannulas can each be inserted in an inclined angle i.e. an angle a where $0°<a<90°$, normally $10°<a<85°$. If the cannulas are inclined it will be possible to let them point in different directions, and e.g. also point away from the subcutaneously positioned sensor part thereby increasing the distance between each outlet from an inclined cannula to the subcutaneously placed sensor part. The distance between the cannulas is defined as x and x will normally advantageously have a minimum size, the size will depend on several factors such as the type of cannula used e.g. length, diameter and material will be of importance, and also type of medication to be supplied through the cannula will determine the necessary minimum distance between two cannulas. The distance between each cannula and the sensor part 72 is defined as y and y will normally also advantageously have a minimum size. The size of y is determined by the degree of influence the supplied medication has on the sensor measurement i.e. y will depend on which type of medication is supplied, what concentration and form the medication is delivered in and e.g. to what depth the medication is supplied and in what depth the sensor part registers a signal.

The two cannulas will normally not be delivering medication to the patient simultaneously. The object of having two cannulas is to be able to retract one cannula while inserting another cannula and still be using the same patch and e.g. also the same sensor. This feature will increase the service life of a patch including both cannula and sensor as the cannula normally will have to be retracted after 3 days while the sensor normally can stay inserted in 6-10 days. It is indicated at FIG. 10 how cannula 22a is inserted or just has been inserted while cannula 22b, at the same time or just after cannula 22a has been inserted, is retracted to such an extend that the cannula 22b is no longer in contact with the former insertion site and the patients skin.

Figure 11:
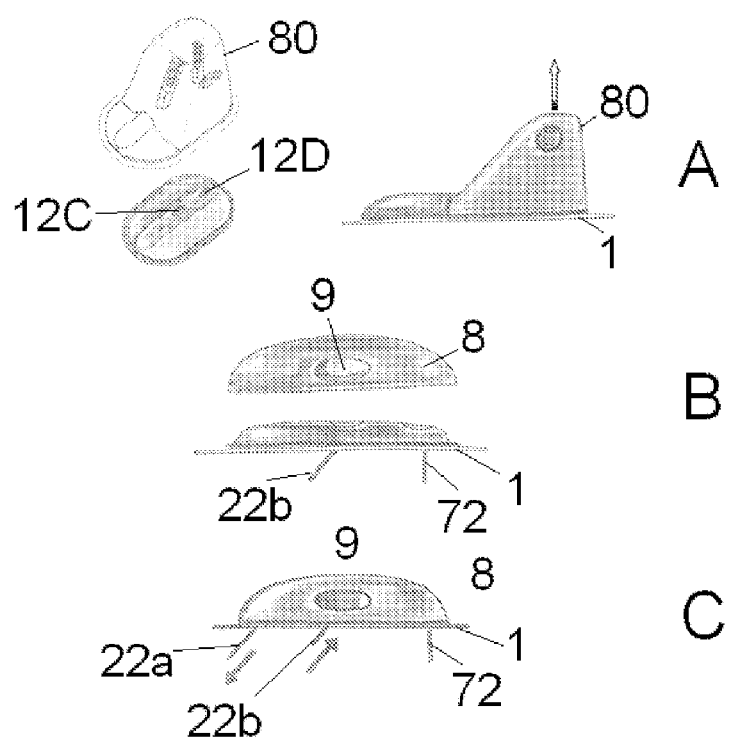
FIG. 11 illustrates how to use the device of FIG. 10.

FIG. 11 shows a sequence of steps of how to use a device as shown in FIG. 10.

FIG. 11A:
Step 1: The patch including a base part 1 provided with an opening 12C for at least one cannula 22b to be inserted with an inserter 80 and an opening 12D for a sensor part is attached to the surface of the patients skin e.g. by a mounting pad 2 which has been adhered or welded to the base part 1. An inserter 80 might be attached to the patch at delivery or the user might have to position an inserter 80 on the patch in order to be able to insert the first cannula 22b and the sensor. Also, two different inserters might be used for inserting respectively the first cannula and the sensor part.
Step 2: The inserter 80 or each of the two inserters inserting respectively the first cannula 22b and the sensor part 72 is/are activated and the subcutaneous parts are positioned. Afterwards, the inserter(s) are removed and disposed of.

FIG. 11B:
Step 3: The patch including the base part 1 and a mounting part is now firmly secured to the patient's skin and the primary subcutaneous units are in working position. The user or the patient can then place a delivery device 8 including reservoir, pumping facilities and controller means on the base part, thereby putting the delivery device to work.

FIG. 11C:
Step 4: After a period of e.g. 2-3 days, the first cannula 22b is retracted and the second cannula 22a having been kept under sterile conditions inside the base part is inserted, thereby making it possible to use the patch for another 2-3 days.

Figure 12:
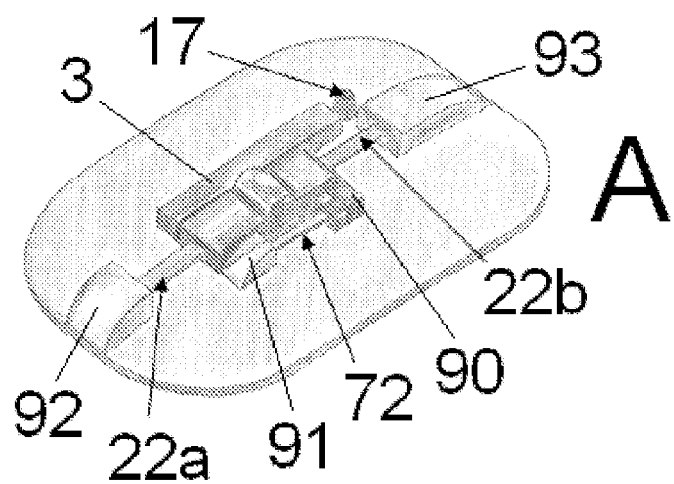
FIG. 12 shows an embodiment of a base part having two cannulas seen from above.
Figure 12:
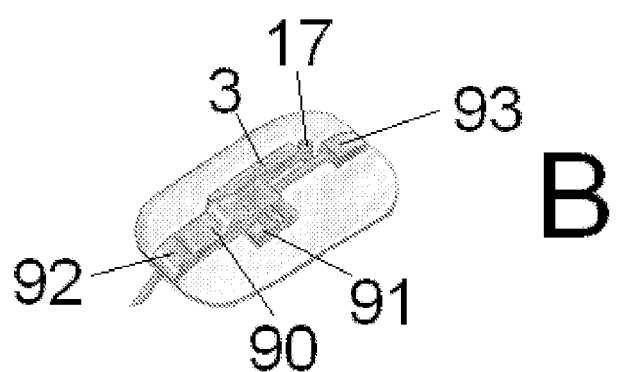
Figure 12:
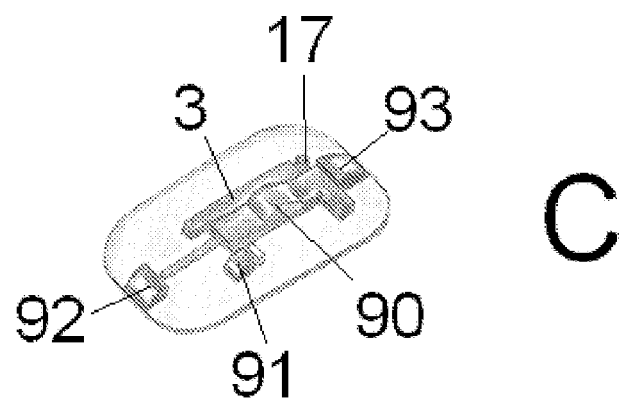
Figure 13:
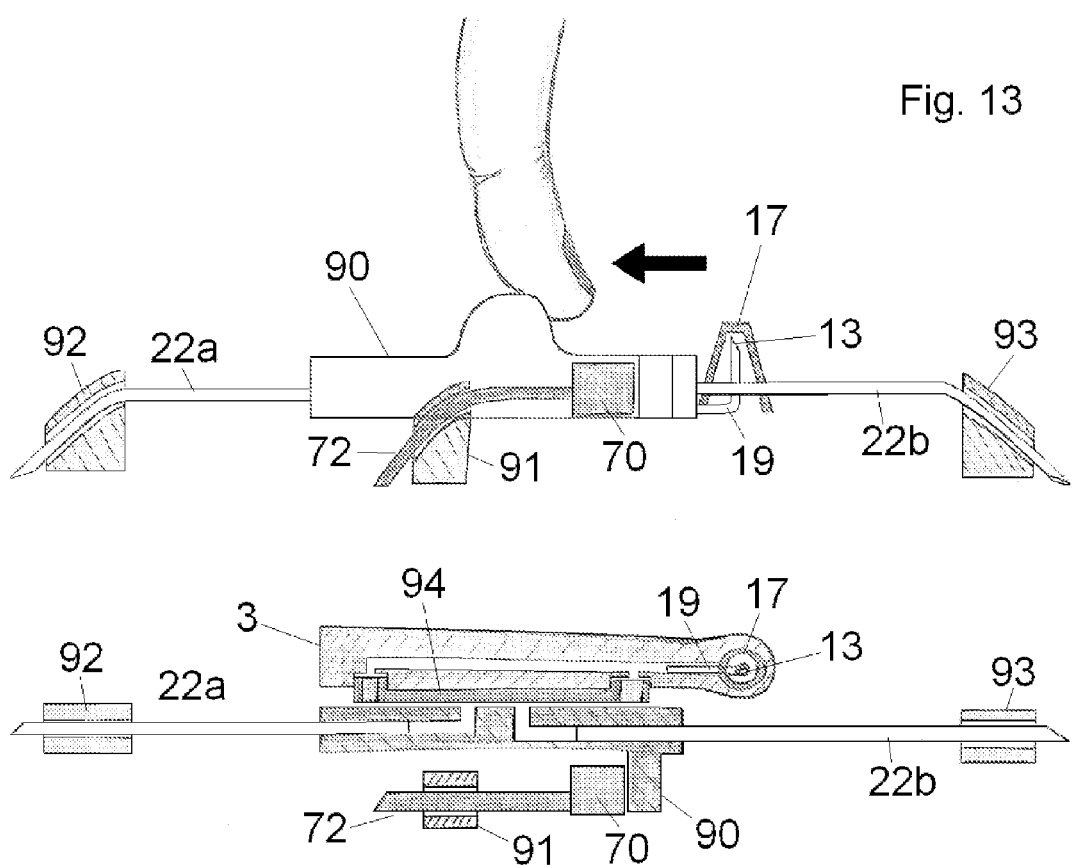
FIG. 13 shows the same embodiment of a base part as FIG. 12 seen from the side.

FIGS. 12 and 13 shows an embodiment of a base part which can perform the 3 steps described above although no inserter needs to be used with the present embodiment. FIG. 12 shows the embodiment in three different states. FIG. 13 shows first the base part in a side view and secondly in a cut-through view from above which allows the viewer to see the flow paths inside the device.

The embodiment comprises an inlet opening 13 through which medication from a reservoir can enter. This inlet opening is also the inlet opening of the second fluid path. The inlet opening 13 is protected with a membrane 17 to prevent contamination with microorganisms. The second fluid path further comprises the connection part 3 provided with both a connector needle 19 and which at a pointy end is protected by the bubble shaped self closing membrane 17. A reservoir positioned within the delivery device can also be provided with a bubble shaped self closing membrane being part of the first fluid path as a first fluid path between the delivery device and an inlet on the base part can be established providing transfer of medication e.g. insulin, other medication or nutrients from the reservoir to the base part via a connector part 3 when the delivery part is attached to the base part. As both parts are provided with self closing membranes it will be possible to separate the two units from each other and rejoin them at a later time without the connection part 3 and thereby the patient being contaminated.

Fluid from a reservoir in the delivery part will enter into the connection part 3 through the inlet opening 13; the connection part 3 is stationary relative to the patch or surface plate 1. The connection part 3 has two outlets for fluid which makes it possible to establish two different second fluid paths, through the first outlet fluid can be delivered to a first inlet in a movable part 90 and from this movable part 90 the fluid is guided to a first cannula 22a where the first of the second fluid paths end. Through the second outlet fluid can be delivered to a second inlet in the movable part 90 and from this movable part 90 the fluid is guided to a second cannula 22b where the second of the second fluid paths end. The first outlet respectively the second outlet from the connection part 3 and the first inlet respectively the second inlet of the movable part 90 though have to be positioned right in front of each other in order for fluid to be transferred from one unit to the other. In FIG. 13 the movable part 90 is in a neutral position where the fluid cannot flow from the connection part 3 to the movable part 90 via any of the possible path ways. Between the connection part 3 and the movable part 90 is placed a gasket 94, this gasket is stationary positioned relative to the connection part 3 and the movable part 90 slides along the surface of the gasket 94. As the gasket 94 is squeezed in between the connection part 3 and the movable part 90, the gasket 94 makes sure that no fluid leaks between the two objects.

The embodiment of FIGS. 12 and 13 also comprises first guiding means 92 for the first cannula 22a, second guiding means 93 for the second cannula 22b and third guiding means 91 for the sensor part 72.

In a first state which is the state the device is delivered in, the movable part 90 is in a central position where neither of the cannulas 22a and 22b nor the sensor part 72 is protruding from the surface of the base part facing the patient when the base part is mounted on the patient's skin. This state is shown in FIG. 12A and FIG. 13.

In a second state the device has been activated, the user has pushed the movable part 90 as far to the left as possible and the first cannula 22a and the sensor part 72 are in fully forward positions while the second cannula 22b is in a fully retracted position. As the cannula 22a is made of a flexible and self-penetrable material the cannula will due to the change in direction caused by the first guiding means 92 penetrate the patient's skin in an angle around 45°. Also the sensor part 72 is made of a flexible and self-penetrable material which due to the third guiding means 91 is also directed to a subcutaneous position in a desired angle. When the sensor part is in its end position, contacts of the sensor part can get in conducting contact with electrical parts of the delivery device which contact is established when the delivery part is mounted on the base part. The activation of this state is illustrated in FIG. 13 by the arrow and the finger and the resulting state is shown in FIG. 12B.

In a third state the user pushes the movable part as far to the right as possible which movement result in that the first cannula 22a is brought to its fully retracted position where it has no contact with the former insertion site while the sensor part 72 stays in the subcutaneous position as the sensor part is not connected to the movable part 90 in such a way that it will get pulled back to its start position. The second cannula 22b is brought to its fully forward position by the movable part 90 and as the second cannula 22b is also made of a flexible and self-penetrating material, the second cannula 22b will cut a subcutaneous path in the patients skin and the second guiding means 93 determines the direction of this path which in the actual embodiment is around 45°.

When the second cannula needs to be removed from the insertion site, it will be necessary to remove the whole patch including the subcutaneously positioned sensor part. The patch or base part can be replaced with a new base part at another position on the patient's skin, but the delivery part can be re-used for several base parts.

Figure 14:
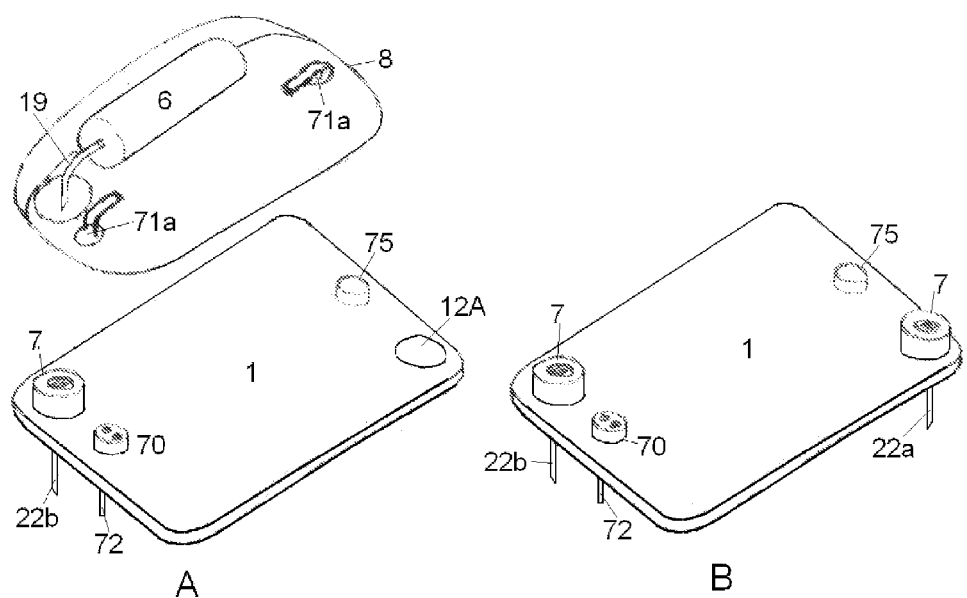
FIG. 14 shows an embodiment of a base part provided with two separated receiving positions for cannulas.

FIG. 14 shows an upper view of an embodiment of a base part provided with two separated positions for cannulas. Separated positions means that the two positions where cannulas can be inserted are placed with a distance x between the outer circumference of the cannula parts, where x>0.

Left half of FIG. 14 shows a base part 1 in a first state where a first cannula part 7 with a cannula 22b has been inserted. Above the base part 1 is shown a delivery part 8 which is ready to be mounted on the base part 1. The delivery part is detachable which means it can be fastened to the base part 1 and released again as often as the user wishes. The delivery part 8 comprises a reservoir 6 which reservoir 6 has an outlet connected to a connector needle 19, fastening means are not shown in FIG. 14. When the delivery part 8 is pushed against the base part 1a first fluid path will be formed as the connector needle 19 of the delivery part will penetrate the top opening of the cannula part 7 and permit a fluid to flow from the reservoir 6 to the base part 1. A second fluid path is constituted by the open room inside the cannula housing as this open room provides transfer of fluid from the outlet of the first fluid path i.e. the connector needle 19 to the open end of the tube shaped cannula 22b which is embedded and secured to the inside of the body of the cannula part 7. The volume of this open room is considered to be so little that plug-flow is still obtained. In the first state the sensor part 70 has also been inserted, the cannula part 7 and the sensor part 70 can be inserted with each an inserted adapted to each part and position after the base part 1 has been attached to the patients skin, or the two parts 7 and 70 can be inserted with one common inserter after the base part 1 has been attached to the patients skin, or the two parts 7 and 70 can be attached to the base part 1 during manufacturing which means that the user will have to place the base part 1 and insert the two subcutaneous units 22b and 72 in one action. In FIG. 14 the see-through embodiment of the delivery part 8 illustrates how the internal parts of the delivery part 8 are positioned. The delivery part 8 also comprises two contacts 71a which contacts 71a create a signal path for the sensor part 70 regardless of the position of the delivery part 8 relative to the base part 1. One of the two contacts 71a rests against a dummy 75 which dummy 75 supports the delivery part 8 in the same way as a sensor part 70 but at a lower price.

Right half of FIG. 14 shows a base part 1 in a second state where a second cannula part 7 with a cannula 22a has been inserted through an opening 12A in the base part 1 at a second position. A fluid path to the cannula 22a at the second position can be obtained by turning the delivery part 8 180° relative to the position shown at the left half illustration. I.e. a changed fluid path is obtained by changing the position of the delivery device 8 relative to the base part 1. Regardless of the position of the active cannula part 7, signals are obtained and sent via the same sensor part 70; the sensor part 70 is though connected to the delivery part 8 via another contact 71a.

Figure 15:
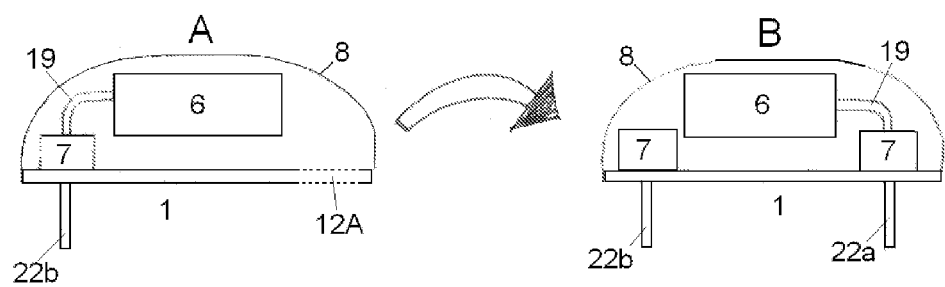
FIG. 15 shows a side view of an embodiment of base part having two separated positions for cannulas and a delivery part mounted in each of these two positions.

FIGS. 15A and 15B show a side view of an embodiment of base part having two separated positions for cannulas and a delivery part mounted in each of these two positions. The sensor part is not shown in this embodiment. As the embodiment of FIG. 4, the fluid path is changed by changing the position of the delivery part. In FIG. 15A the delivery part 8 is in a first state where the cannula needle 19 of the delivery part 8 is penetrating a septum in a first cannula part 7 having a subcutaneous cannula 22b thereby providing a first and a second fluid path. In FIG. 15B the delivery part 8 is in a second state where the cannula needle 19 of the delivery part 8 is penetrating a septum in a second cannula part 7 having a subcutaneous cannula 22a thereby providing a new second fluid path. The second state for the delivery part 8 is obtained by turning it 180° in a horizontal plane relative to the base part 1. If the signal path between the delivery part 8 and the base part 1 is provided through a flexible conduct which e.g. can be rolled up inside the housing of the delivery part 8, it would be possible to connect the reservoir of the delivery part 8 to more than two cannula parts 7 while still maintaining signal contact with a single sensor.

Figure 16:
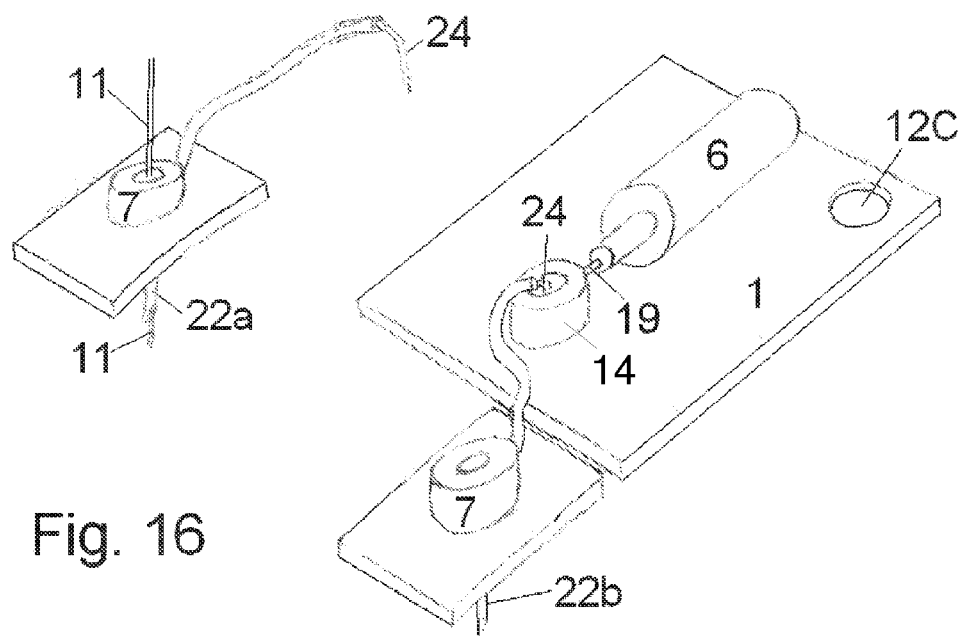
FIG. 16 shows a embodiment of a base part combined with a releasable site for a cannula.

FIG. 16 shows an embodiment of a base part 1 which base part 1 is combined with two releasable sites for a cannula. The number of cannulas sites used with each sensor provided base part could be more than the two cannula sites used for illustration, the number of independent sites has no upper limitation as such.

According to this embodiment a base part 1 comprises a receiving portion 14 comprising the not shown inlet opening for the first fluid path. The first fluid path is established in the receiving portion 14; a connector needle 19 from the reservoir 6 allows fluid to enter the receiving portion 14 when the connector needle 19 is forced through a protective septum which closes a (not shown) side opening in the receiving portion 14 and a cannula connector needle 24 establishes a second fluid path between the base part 1 and a subcutaneously positioned cannula 22b or 22a. A sensor part 70 is to be positioned in an opening 12C and according to this delivery part 8 the reservoir 6 is positioned before and separately from the electrical part and the housing.

When a user is to start using the embodiment of FIG. 16, the base part 1 is first positioned and attached to the patient's skin via a not shown mounting surface or mounting part. After having secured the base part 1 to the patients skin the user can position the reservoir 6, if this is not already a part of the base part 1. Then the user places a cannula site on the patients' skin, when provided with a soft cannula 22 the cannula site has to be positioned with an insertion needle 11 which insertion needle might be part of a manual or an automatic inserter. After having positioned the first cannula site, a second fluid path is established by pressing a cannula connector needle 24 through a top septum in the receiving portion 14. The cannula connector needle 24 is connected to the cannula site via a flexible tube through which the medication from the reservoir 6 which has entered the receiving portion 14 can flow. After 3 days or if a problem such as inflammation or leakage arises with the first cannula site, the site is disconnected by retracting the cannula connector needle 24 from the receiving portion 14 where after the cannula site can be removed from the patients skin, then a second cannula site with a soft cannula 22a is mounted on the patients skin and a new second fluid path is established by pressing the cannula connector needle 24 of this cannula site through the top septum of the receiving portion 14 of the base part 1.

Figure 17:
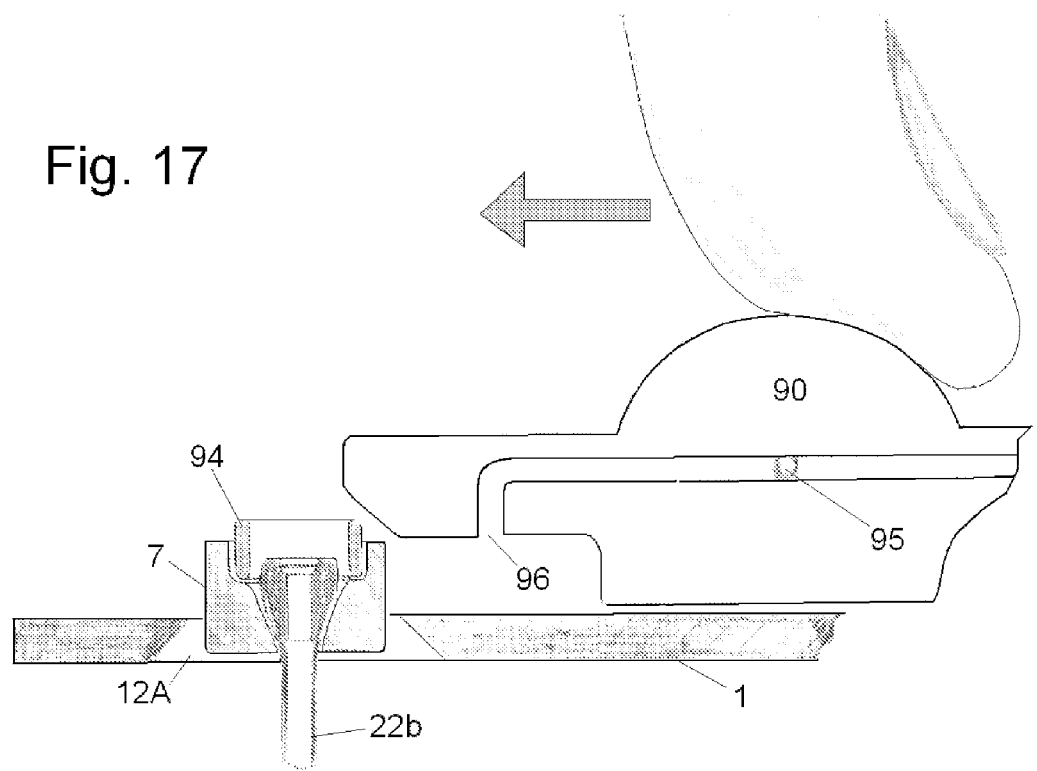
FIG. 17 shows an embodiment of a base part where the fluid path is established by pushing a common part.
Figure 18A:
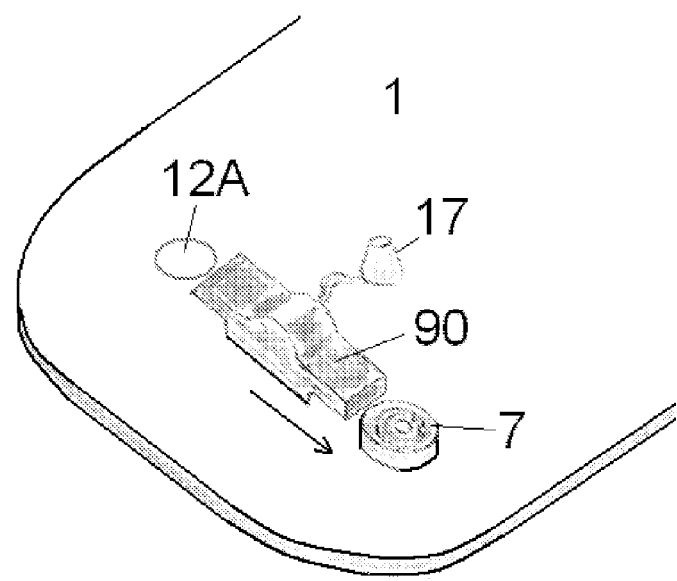
FIG. 18A-B show an embodiment of a base part provided comprising a second fluid path having a slidable unit.
Figure 18B:
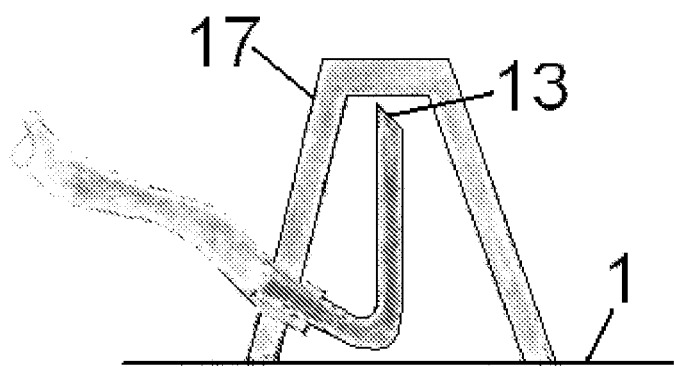

FIGS. 17, 18A and 18B shows yet another embodiment of a base part provided with more than one cannula part. FIG. 17 shows a cut-through side view of the embodiment, FIG. 18A shows an upper view of the embodiment and FIG. 18B shows an enlargement of the coupling part establishing a first fluid path with the delivery part.

According to this embodiment of a base part, a second fluid path can be established by pushing a moving part 90 to a first or a second position from a central closed position which central closed position of the movable part 90 allows for insertion of either one of two cannula parts 7. The moving part 90 is an unreleasable part of the base part 1 i.e. it cannot be removed from the base part but only be moved between different positions. The movable part 90 has an inlet 95 for fluid; the inlet 95 is unreleasably connected to a flexible tube connecting the movable part 90 to an inlet opening 13 for the second fluid path. The inlet opening 13 is the end of a penetrating cannula protected by a bubble shaped membrane 17. The membrane 17 is penetrated by the cannula when a delivery part is pressed against the base part, when the delivery part is pressed against the base part a first fluid path is established between the reservoir of the delivery part and the base part and fluid can flow directly to the movable part 90, fluid can only flow from the movable part 90 to a cannula part 7 if the movable part 90 is pushed to contact with a cannula part 7 as illustrated with the arrow on FIG. 18A.

Common for all the embodiments are that the base part has one inlet for fluid and one or more outlets for fluid i.e. the medication enters at one position via the inlet of the second fluid path and the second fluid path is then provided with one or more outlets to one or more cannula parts. Normally, there is no "reservoir" after the fluid has left the especially protected reservoir 6 of the delivery part which is used to store the fluid medication before and during use, after the fluid has left this designated reservoir 6 the fluid travels in a plug-flow assuring that all fluid has a well-defined short residence time inside the base part.

The invention claimed is:

1. A base part for subcutaneous introduction of a cannula, the base part comprising:
   a connection part comprising an inlet opening adapted to receive a first flow of fluid from a delivery part to a first outlet opening, and a second flow of fluid from the delivery part to a second outlet opening, wherein said delivery part comprises a reservoir;
   a moveable part, which moves relative to the connection part, the movable part having at least two different positions:
      a first position forming a first fluid path from the first outlet opening of the connection part to a first inlet of the moveable part and then to a first cannula or sensor; and
      a second position forming a second fluid path from the second outlet opening of the connection part to a second inlet of the moveable part and then to a second cannula or sensor,
   wherein the base part comprises a first guiding means for causing a first change in direction of about 15 to about 85 degrees for a distal part of the first cannula or sensor after the moveable part has been moved into the first position, and a second guiding means for causing a second change in direction of about 15 to about 85 degrees for a distal part of the second cannula or sensor after the moveable part has been moved into the second position.

2. The base part according to claim 1, wherein the inlet opening is protected by a protective sealing membrane.

3. The base part according to claim 1, comprising a gasket positioned between the connection part and moveable part wherein the gasket is stationarily positioned relative to the movable part.

4. The base part according to claim 1, wherein the first cannula and the second cannula comprise a soft and flexible material or a hard and rigid material.

5. The base part according to claim 4, wherein the first cannula and the second cannula comprise the soft and flexible material.

6. The base part according to claim 5, wherein the first cannula and the second cannula each comprise an elastomer.

7. The base part according to claim 1, wherein the first position results in penetration of skin by the first cannula, and wherein the second position results in penetration of skin by the second cannula.

8. The base part according to claim 1, wherein the first change in direction is about 45 degrees.

9. The base part according to claim 1, wherein the second change in direction is about 45 degrees.

* * * * *